United States Patent [19]
Shaw et al.

[11] 3,969,929
[45] July 20, 1976

[54] DRILL MODULE FOR BOREHOLE STRESS MEASURING INSTRUMENT

[75] Inventors: Garrett D. Shaw, Rancho Palos Verdes Peninsula; Clyde E. Williamson, Torrance, both of Calif.

[73] Assignee: TRW Inc., Redondo Beach, Calif.

[22] Filed: June 9, 1975

[21] Appl. No.: 585,428

[52] U.S. Cl. .................................. 73/88 E; 73/151
[51] Int. Cl.² ....................................... E21B 49/00
[58] Field of Search ............... 73/88 E, 151, 88 A, 73/71.3; 350/3.5; 408/131

[56] References Cited
UNITED STATES PATENTS

| | | | |
|---|---|---|---|
| 3,002,404 | 10/1961 | Estabrook | 408/131 X |
| 3,557,886 | 1/1971 | Cobbs | 73/88 E X |
| 3,563,652 | 2/1971 | Powell et al. | 73/88 A X |

Primary Examiner—Jerry W. Myracle
Attorney, Agent, or Firm—Daniel T. Anderson; Donald R. Nyhagen; Edwin A. Oser

[57] ABSTRACT

A drill module for use in a holographic borehole instrument which is operable to determine the stress in the wall of a borehole by recording successively on the same holographic recording medium two holograms of a selected surface region of the wall and, in the interval between the two recordings, drilling a stress relief hole in the wall in stress relieving relation to the selected surface region to produce on the recording medium a double exposure hologram containing holographic information representing the stress. The drill module embodies a drill which is normally retracted from the field of view of the holographic system to permit unobstructed holographic recording of the selected wall surface region and which is extended into the field to drill the stress relief hole in the interval between the two holographic recordings.

11 Claims, 13 Drawing Figures

DRILL MODULE FOR BOREHOLE STRESS MEASURING INSTRUMENT

The invention herein described was made in the course of or under a contract or subcontract thereunder, (or grant), with the Department of the Air Force.

RELATED APPLICATIONS

Reference is made herein to copending applications entitled "In-situ Stress Measuring Apparatus and Method," filed Dec. 9, 1974, Ser. No. 530,626 by Thomas J. Ahrens, Pravin G. Bhuta, and Robert L. Johnson; "Hologrpahic Instrument for Measuring Stress in a Borehole Wall," filed June 2, 1975, Ser. No. 585,269, by Jerold L. Jacoby, Garrett D. Shaw, Pravin G. Bhuta, and James L. Schmidt (TRW Docket 75-092); and "Optical Module for Borehole Stress Measuring Instrument," filed June 2, 1975, Ser. No. 584,806 by Jerold L. Jacoby and Clyde E. Williamson (TRW Docket 74-145).

BACKGROUND OF THE INVENTION

1. Field of the Invention

This invention relates generally to the field of stress measurement and mor particularly to a novel drill module for use in the borehole stress measuring instrument of the above-mentioned copending application, Ser. No. 584,806, (TRW Docket 74-145).

2. Prior Art

An important, and in many cases crucial, requirement in many geological activites is the determination or measurement of the in-situ field, including both stress magnitude and stress direction, in geological structures. Some of these geological activities are utilization of geothermal energy;
tunnel excavation;
discrimination of teleseismic signals to determine their origin (earthquake or expolsion); and
earthquake prediction.

Utilization of geothermal energy, for example, involves drilling of boreholes or passages into subterranean rock formations which are exposed to geothermal heating and circulation of water through such passages for heating of the water by heat transfer from the rock. Efficient heat transfer from the rock to the water requires fracturing of the rock walls of the water passages. Efficient and economical fracturing of the rock, in turn, necessitates a precise knowledge of the principal stresses in the rock.

Knowledge of the basic data related to rock properties is also required in tunnel excavation. Among the required data is information pertaining to the in-situ stress field in the rock. Such information is required to both determine the stability of the tunnel wall and insure the safety of tunnel occupants. As tunneling proceeds to greater depth, in-situ stress field measurements at operational depths become important to production planning. The risk of rock bursts and cave-ins in a tunnel is, in general, dependent on the stability of the surrounding stress field (tectonic and overburden) and its long-term response to the presence of the tunnels. Thus one primary requirement, in addition to knowledge of the underground geology, in the safe design of tunnels, is the determination of both the magnitude and direction of the in-situ stress fields.

A variety of in-situ stress measurement techniques and devices have been devised. Examples of such techniques and devices are described in the following publications:

Aggson, Jr. R., "Bureau of Mines Borehole Deformation Gage for Determining In-Situ Stress," *Bureau of Mines Information* Circular 8585, July 25, 1972.

Pallister, G. F., N. C. Gay and N. G. W. Cook, "Measurement of the Virgin State of Stress in Rock at Depth," *Proc. of the Second Congress, International Society of Rock Mechanics*, Belgrade, 25, 1970.

Merrill, R. H., "In-Situ Determination of Stresses by Relief Techniques," in *State of Stress in the Earth's Crust*, W. R. Judd, ed. 343, Elsevier Co., 1964.

These and other previously available in-situ stress measurement techniques, however, do not provide a "complete measure" of the state of stress in the vicinity of the borehole, i.e. tunnel or vertical bore. For Example, the Bureau of Mines borehole deformation gage, which is currently the best available technique, provides sufficient information to calculate the state of stress in a plane normal to the borehole. In order to obtain a measure of all the components of stress, borehole deformation measurements would be required from three non-parallel boreholes. In calculating the stability of openings, it is also necessary to have a measure of the in-situ stress (tectonic plus overburden) parallel to the axis of the vertical borehole. Disadvantages of the Bureau of Mines borehole deformation gage are that the state of stress at a point is difficult to measure even using three holes and additional expenses are incurred in drilling three holes rather than one. Even after three holes are drilled, the technique provides a measure of three-dimensional average ground stress components because of the nature of the instrumentation used. If this technique were utilized to obtain a measure of the in-situ stresses as a function of depth, the expense incurred would be large, especially if the application is for the design of a deep mine. It should be pointed out, however, that the United States Bureau of Mines gage is a working instrument.

The earlier mentioned copending application Ser. No. 530,626, discloses an improved technique for determining stress in load-bearing structures, both manmade and geological structures. Simply stated, this technique involves recording successively on the same holographic recording medium two holograms of a selected surface region of the load-bearing structure and, in the interval between the two recordings, forming a stress relief in the stucture in stress relieving relation to the selected surface region. The resulting composite hologram recorded on the medium is a double exposure hologram containing holographic information which represents the displacement of the surface. Both stress direction and stress magnitude in the structure may be derived from these data, using independent knowledge of the elastic constants of the sturcture medium. The holographic information contained in the double exposure hologram is a fringe pattern resulting from the deformations or displacements which occur at the surface of the structure between the first and second holograms by virtue of the stress relief formed in the structure. According to the preferred practice of the invention, the stress relief is formed by drilling a hole into the structure within its selected holographically imaged surface region.

Copending application Ser. No. 585,269 (TRW Docket 75-092), discloses a holographic instrument for practicing the above method of stress measurement in a borehole to determine the stress in the wall of the hole. This instrument has a modular construction including an upper holographic optics module and a lower drill module which are releasably coupled end to end. The holographic optics module includes a holographic recording system having a field of view along an optic axis transverse to the longitudinal axis of the instrument at the lower end of the optics module.

In operation, the borehole instrument is lowered to a selected depth in a borehole, whereupon the optics and drill modules are anchored and sealed to the wall of the hole and then uncoupled from on another. The space between the wall and instrument may be flushed to provide a clear medium within the space. The instrument if then operated to record a first hologram of the borehole wall region within the field of view of the halographic recording system, then drill a stress relief hole in this wall region, and finally record a second hologram of the wall region. The two holograms are recorded on the same recording medium to produce a double exposure hologram or holographic interferogram containing holographic information representing the stress field in the borehole wall region.

The holograms are recorded by holographic recording system of the optics module. The stress relief hole is drilled by the drill module, which is uncoupled from the optics module during the instrument operation, as noted, to prevent the drilling operation from disturbing the optics module in the interval between the two holograms as required for double exposure holography.

SUMMARY OF THE INVENTION

This invention provides a drill unit or module for the borehole stress measuring instrument of the copending application Ser. No. 585,269 (TRW Docket 75-092). As just noted, the drill module is located at the lower end of the holographic optics module of the instrument and is operable to drill a stress relief hole in borehole wall region of interest in the interval between recording two succesive holograms of the wall region to produce a holographic interferogram containing information representing the stress field in the wall region.

The drill module of the invention has a housing mounting at its upper end coupling means for releasably coupling the housing to the lower end of the holographic optics module of the borehole holographic instrument. Mounted on the housing for extension and retraction along a first direction line parallel to and a second direction line transverse to the longitudinal axis of the housing is a drill head for mounting a drill with its axis parallel to the second direction line of extension and retraction of the head. Actuator means are provided for extending and retracting the drill head along the two direction lines.

In operation of the drill module in the borehole instrument, the drill head is initially retracted along both of its direction lines of extension and retraction. In this retracted position, the drill head is situated out of the field of view of the holographic optics module of the instrument to permit recording of holograms of the borehole wall region of interest within the field of view in the manner just mentioned. Following recording of the field of two holograms of a wall region with the drill head retracted, the head is initially extended upwardly along its first direction line parallel to the longitudinal axis of the borehole instrument to a position opposite the wall region of interest, and then outwardly toward this wall region along the second direction line transverse to the longitudinal axis to drill a stress relief within or in stress relieving relation to the wall region. The drill head is then retracted in the reverse order along the two direction lines to its retracted position to permit recording of the second hologram of the wall region. The drill module may also be equipped with means for exhausting drilling debris from the drill.

DESCRIPTION OF THE PREFERRED EMBODIMENTS

Figure 1A:
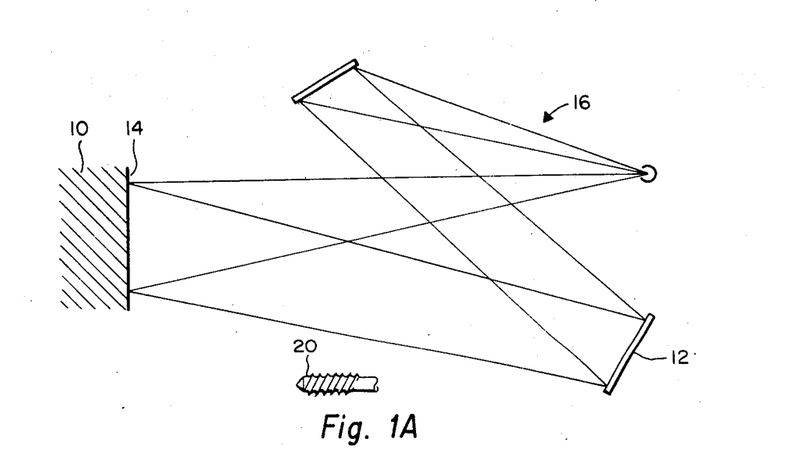
FIGS. 1A, 1B, and 1C illustrate the method of stress determination disclosed in copending application Ser. No. 530,626.
Figure 1B:
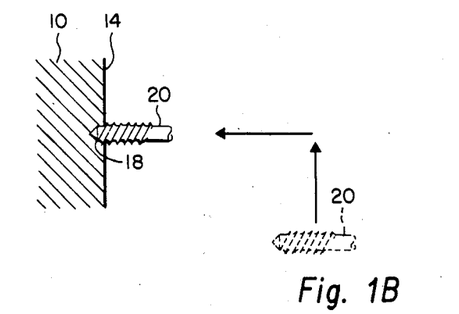
Figure 1C:
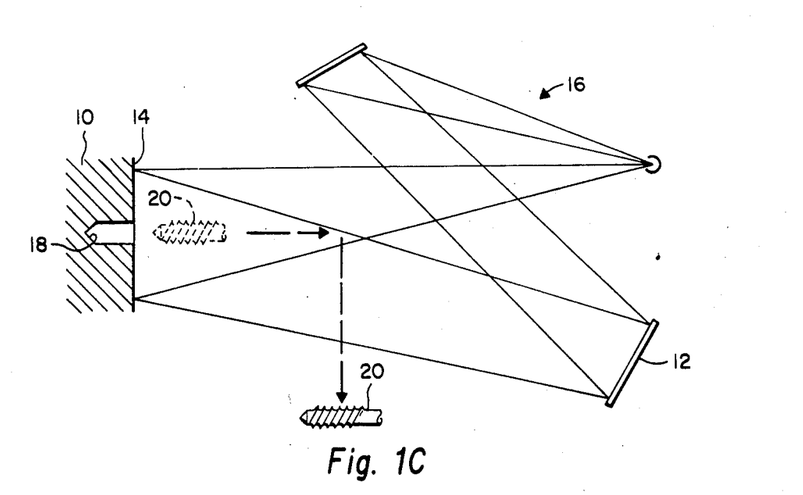

Reference is made first to FIGS. 1A, 1B, and 1C of the drawings illustrating the method of copending application Ser. No. 530,626 for determining stress in a load-bearing structure. In these figures, reference numeral 10 denotes the load-bearing structure of interest. The first step (FIG. 1A) of the method involves recording on a holographic recording medium 12 a first hologram of a selected surface region 14 of the structure. Any suitable conventional or specially designed holographic system 16 may be employed to record the hologram.

The second step (FIG. 1B) of the method involves forming a stress relief 18 in the structure 10 in stress relieving relation to the surface region 14 of interest on the structure. This stress relief may be formed in a number of ways, as by sawing, slicing, acid etching, drilling, or otherwise recessing the structure. In FIG. 1B, the stress relief 18 is a hole which is drilled into the structure by a drill 20. In the context of this disclosure, the above expression "in stress relieving relation to the surface region" means in such relation to the surface region as to cause deformations or displacements to occur within the material of the structure in the vicinity of and at the surface region, the direction and magnitude of which displacements are related to the direction and magnitude of the stress field in the structure in the vicinity of the surface region. In this regard, it will be apparent from the ensuing description that the stress relief may be situated directly within the surface region 14 of simply adjacent the region. The particular stress relief hole shown enters the structure within the surface region 14, and the drill 20 is extendable and retractable into and from its drilling position, as indicated by the solid and broken lines in FIG. 1B, for the reasons explained below.

The third step (FIG. 1C) of the method involves recording on the holographic recording medium 12, by operation of the holographic system 16, a second hologram of the surface region 14 after formation of the stress relief 18. The two holograms recorded on the medium thus constitute a double exposure hologram, or holographic interferogram, containing holographic information which represents the stress field, i.e. both stress magnitude and stress direction, within the structure, and may be converted to data defining the stress direction and magnitude.

Figure 2:
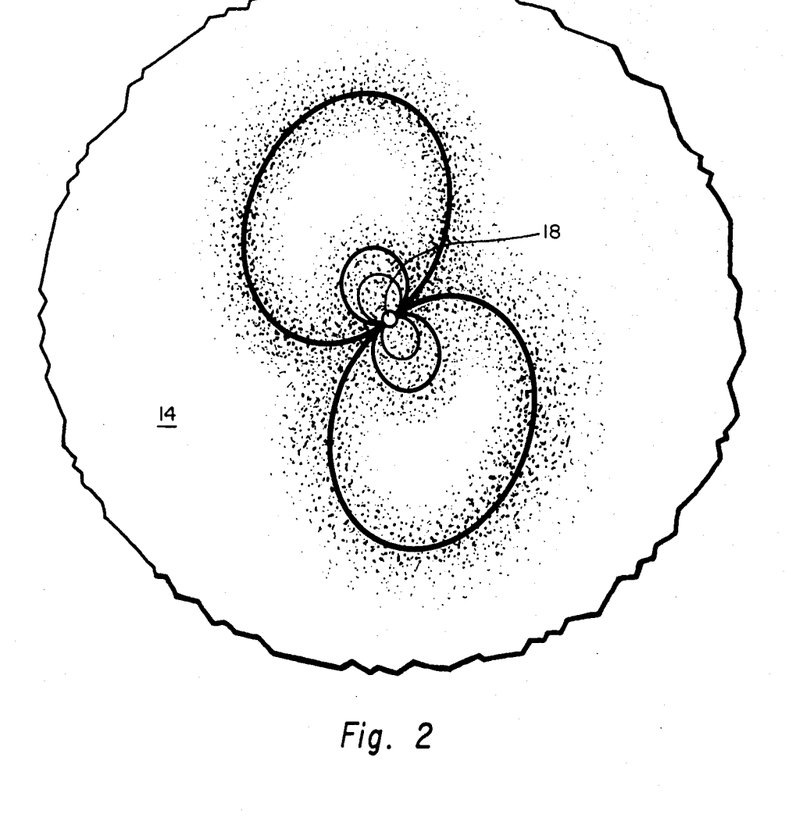
FIG. 2 depicts a holographic image which might be obtained by utilization of the stress determining method.

It will be understood at this point, therefore, that the illustrated method of stress determination involves, essentially, recording successively on the same holographic recording medium two holograms of a selected surface region on the load-bearing structure of interst and, in the interval between the two holographic recordings, forming a stress relief in the structure in stress relieving relation to the selected surface region to produce on the recording medium a double exposure hologram or holographic interferogram containing holographic information representing the stress field in the structure in the vicinity of the surface region. This information is recovered by reconstructing the interferogram. The reconstructed interferogram is a holographic image of the surface region with dark fringes representing the displacements produced at the surface by the stress relief. These surface displacements and hence their resulting fringes are indicative of the stress field, i.e. stress direction and magnitude, within the structure in the vicinity of the surface region. FIG. 2 illustrates a typical fringe pattern produced by the practice of the invention on a flat granite slab which is stressed in an edgewise direction.

Interpretation of the fringe pattern obtained from the interferogram may be accomplished using the technique described by E. B. Aleksandrow and A. M. Bonch-Bruevich in an article entitled "Investigations of Surface Strains by the Holographic Techniques,"published in Vol. 12, No. 2, page 258 of *Soviet Physics, Technical Physics*. Using this technique it can be shown that the dark fringes covering the surface of the borehole are located whereever the condition $$\rightarrow \vec{\delta} \cdot (\vec{s} + \vec{c}) = \frac{(2n \pm 1)}{2} \lambda \qquad (1)$$

is satisfied; where
  $\delta$ = displacement vector representing the deformation of the borehole wall at the point on its surface
  $\lambda$ = wavelength of the light from the laser used to make and reconstruct the holographic images
  $\vec{c}$ = unit vector in the direction from the object to the illuminating source
  $\vec{s}$ = unit vector in the direction from a given point on the borehole through the hologram, to the observer
  $n$ = interger, $\pm 1$, $\pm 2$, $\pm 3$.

Figure 3:
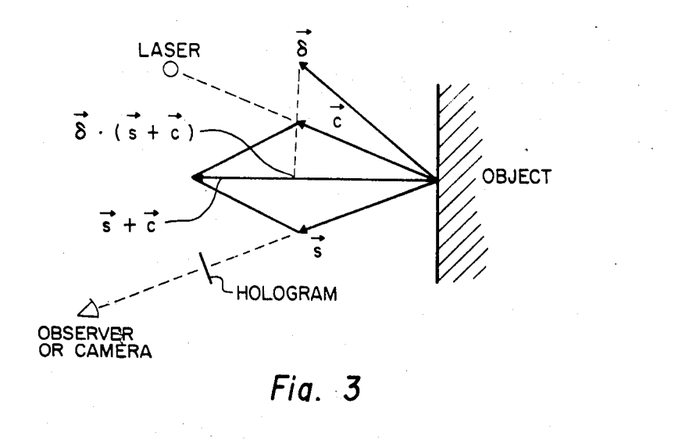
FIG. 3 is a diagram depicting certain aspects of the method.

The term $\vec{\delta} \cdot (\vec{s} + \vec{c})$ is best understood using the vector diagram depicted in FIG. 3. The term $(\vec{s} + \vec{c})$ represents a vector bisecting the angle between vectors $c$ and $s$ having a length $2 \cos \frac{1}{2} (\vec{s}, \vec{c})$. Hence the term $\vec{\delta} \cdot (\vec{s} + \vec{c})$ represents the component of deflection $\delta_{c,s}$ in the direction of a unit vector bisecting the angle between the viewing and illuminating direction times a factor 2 $\cos \frac{1}{2} (\vec{s}, \vec{c})$. Hence, Equation (1) can be written $$\delta_{c,s} = \frac{(2n \pm 1) \lambda}{4 \cos \frac{1}{2} (\vec{s}, \vec{c})} \qquad (2)$$

Qualitatively, the fringes seen over the object represent lines of constant displacement in the direction of the vector $\vec{c} + \vec{s}$. If parallel light is used to illuminate the object and the angle subtended by the object from the position of the observer is less than 1°, then the vector $\vec{c} + \vec{s}$ can be considered constant for all points on the object surface. This fringe displacement information may be converted to data defining the direction and magnitude of the stress field in the structure in the vicinity of the surface region of interest. It will be understood that the above procedure may be repeated for any number of contiguous surface regions to obtain more extensive stress field profile of the structure. The holography system will be set up at each surface region in such a way as to obtain the conditions stated above and depicted in FIG. 3.

As mentioned earlier, and as is apparent from the description to this point, the described method may be used to determine stress in virtually any load-bearing structure including both man-made or fabricated structures and natural or geological structures. One useful application of the invention involving fabricated structures, for example, is determining stress in aircraft and aerospace structures.

A geological application of the method involves determination of the stress in a subterranean geological formation or structure, such as a subterranean rock structure by drilling a borehole in the structure and determining the stress field in the borehole wall. As will appear from the ensuing description, the stress data obtained may be utilized for various geological purposes, such as those mentioned earlier, i.e. geothermal bore wall fracturing, tunnel excavation, teleseismic signal discrimination, and earthquake prediction. FIGS. 4 through 11 illustrate a holographic instrument 100 according to copending application Ser. No. 585,269 (TRW Docket 75-092) and embodying a drill module according to this invention for use in such a geological application.

Figure 4:
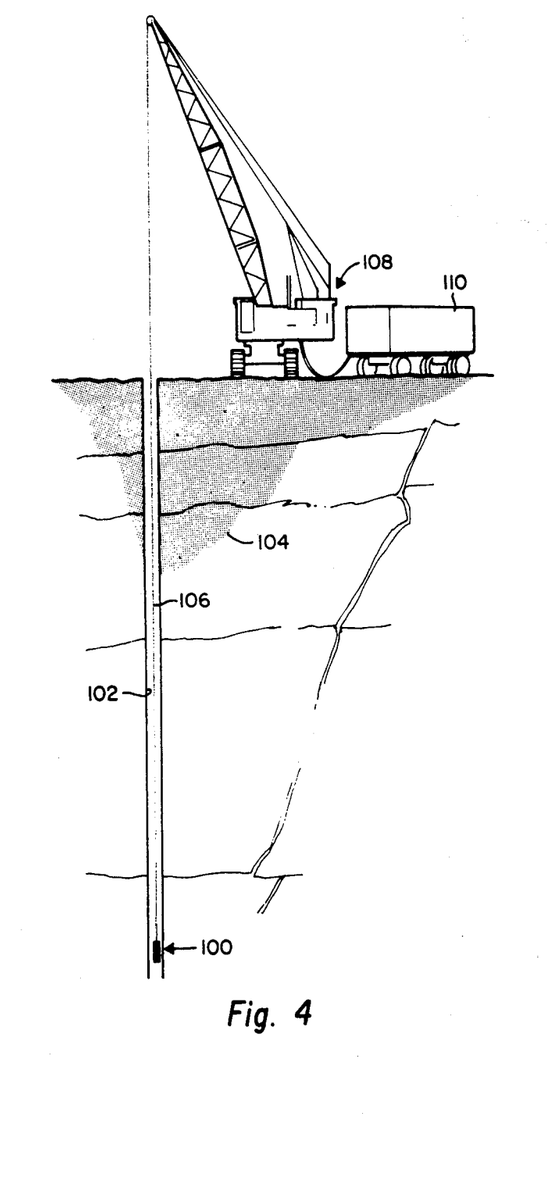
FIG. 4 illustrates the holographic instrument of copending application Ser. No. 585,269 (TRW Docket 75-092), which utilizes the method of FIGS. 1A, 1B, and 1C to determine the stress in a borehole wall.

Referring first to FIG. 4, reference numeral 102 denotes a borehole extending from the surface downwardly through a subterranean geological formation or structure 104 whose stress or stress field is to be determined. Borehole 102, for example, may be a pilot bore which is drilled for the purpose of making the stress determination, a geothermal well bore or passage whose wall is to be fractured, or a borehole for some other purpose.

The holographic instrument 100 is a borehole stress logging instrument which is suspended within the borehole 102 by a cable 106. Cable 106 is supported by a crane 108 having a hoist mechanism by which the instrument may be lowered into and raised from the borehole. Controls and a power source for the instrument are contained in a van 110 at the surface and connected to the stress logging instrument 100 through the hoist cable 106 or a separate cable.

Figure 5:
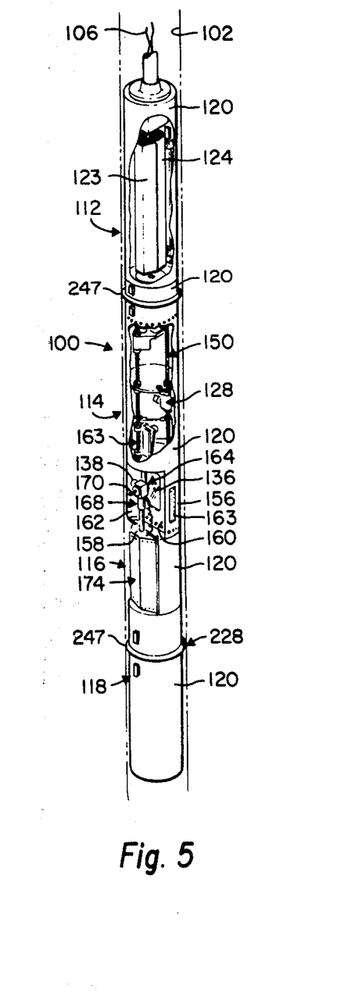
FIG. 5 is an enlarged perspective of the holographic instrument shown in FIG. 4 with parts broken away for clarity.
Figure 9:
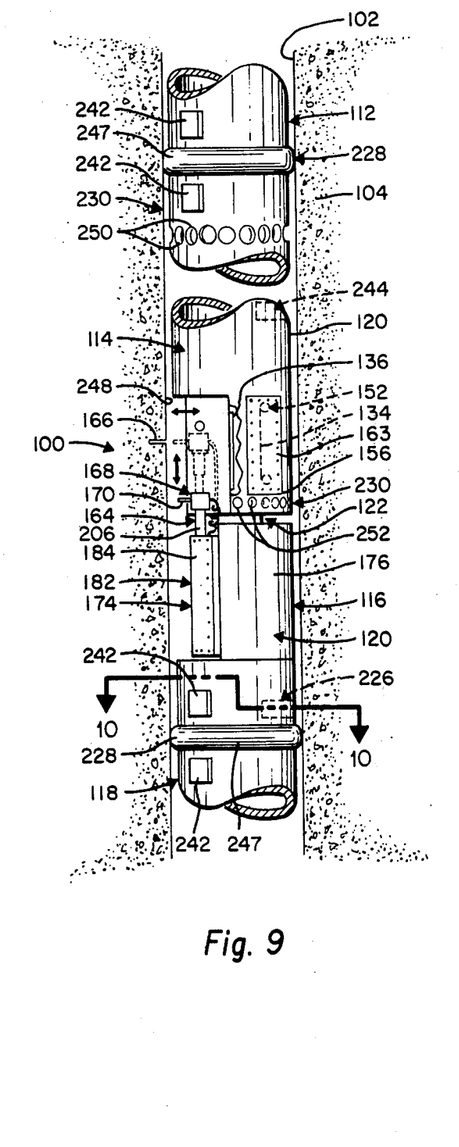
FIG. 9 is an enlarged fragmentary side elevation of the instrument.
Figure 10:
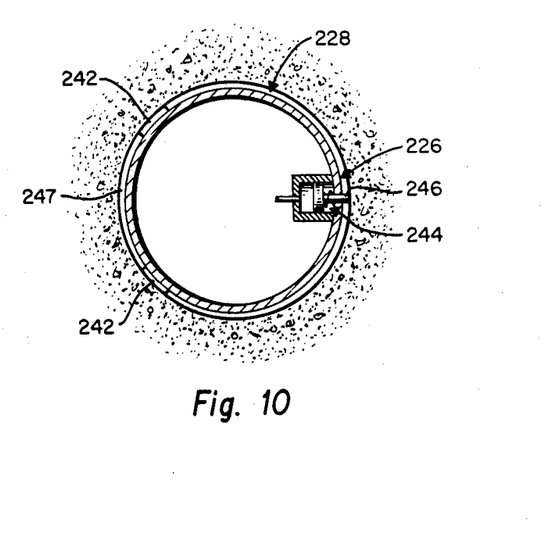
FIG. 10 is an enlarged section taken on line 10—10 in FIG. 9.

Referring to FIG. 5, the holographic stress logging instrument 100 has an elongate cylindrical configuration and is sized to fit quite closely within the borehole 102. The instrument comprises a number of modules arranged end-to-end including, from top to bottom, a laser module 112, an optics module 114, a drill module 116 which constitutes the subject matter of this invention, and a hydraulic power and control module 118. These modules have cylindrical housings 120 of the same diameter and are coaxially joined end to end to form a unitary structure. The housings of the laser and optics modules 112 and 114 are bolted or otherwise rigidly joined to one another and are sealed to form a hermetic housing enclosure. The housings of the drill and control modules 116 and 118 are also rigidly joined to one another. The optics module 114 and drill module 116 are releasably joined by coupling means 122 (FIG. 9).

Mounted within the housing 120 of the laser module 112 is a pulse laser 123, such as a helium-neon laser, and a laser power supply 124. The laser output beam 126 is directed downwardly into the optics module 114 along a path substantially parallel to the longitudinal axis of the module.

Figure 6:
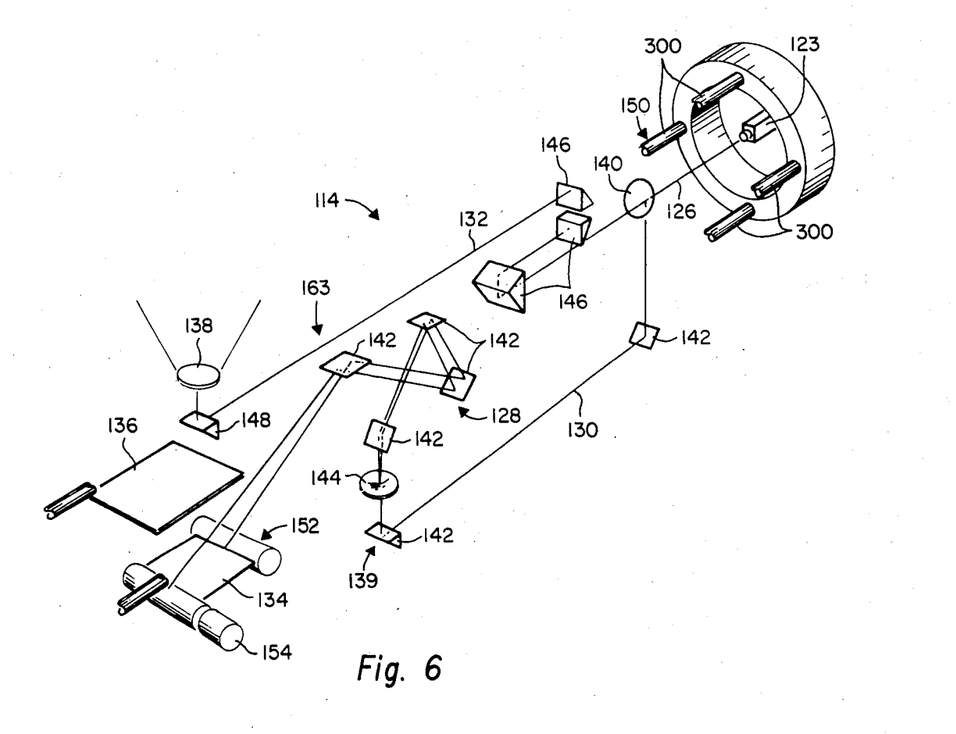
FIG. 6 is a diagrammatic illustration of the holographic optics embodied in the instrument.

The optics module 114 contains holographic optics 128 for splitting the laser output beam 126 into reference and scene beams 130 and 132 directing the reference beam 130 to a holographic recording medium 134 located within the lower end of the module directly behind a laterally facing window 136 in the module housing 120, and directing the scene beam 132 through a window 138 in the lower end of the module housing to the wall of the borehole 102 opposite the window 136. As explained below, the coherent light of the scene beam is reflected from the wall of the borehole through the window 136 to the holographic recording medium 134 and interacts with the coherent light of the reference beam 130 to record on the medium a hologram of the surface region of the borehole wall illuminated by the scene beam.

Any suitable holographic optics may be used in the optics module 114. The particular optics shown comprises a holographic optical unit which constitutes the subject matter of the earlier mentioned copending application Ser. No. 584,806 (TRW Docket 74-145). Accordingly, the illustrated optics will be described only in sufficient detail to enable a complete understanding of this invention. With this in mind, the illustrated holographic optics 128 comprises a beam splitter 140 which splits the laser output beam 126 into the reference and scene beams 130 and 132, optical reflectors 143 which reflects the reference beam through a diverging lens 144 to the holographic recording medium 134, and optical reflectors 146 and 148 which reflect the scene beam 132 through the window 138 to the wall of the borehole 102. Reflector 148 is a prism with a diffuse reflecting surface, and window 138 is a diverging lens which spreads the diffuse reflected light from the prism to illuminate generally uniformly the entire surface region of the borehole wall which is visible to the recording medium 134 through the window 136.

The holographic optics 130 are mounted on a supporting frame 150 within the optics module 114. As explained in the copending application Ser. No. 584,806 (TRW Docket 74-145), this frame includes means for adjusting the optics to provide the proper reference and scene beam path lengths for holographic recording on the recording medium 134 in accordance with this invention. So far as this invention is concerned, it is assumed that the beams have the proper path length.

Holographic recording medium 134 comprises a strip of holographic recording film which is contained within a film cassette 152. This cassette is equipped with a motorized film drive 154 for periodically advancing the film strip through the cassette to expose or uncover successive portions of the strip for holographic recording.

Figure 7:
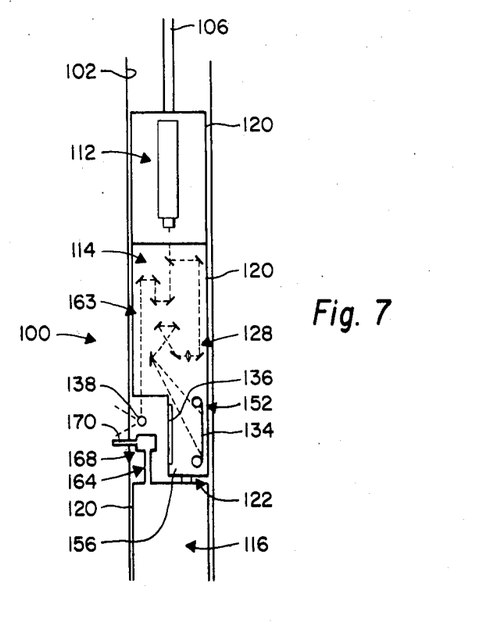
FIG. 7 is a semi-diagrammatic elevational view of the instrument.

As best shown in FIGS. 4, 5, and 7, the optics module housing 120 has a non-circular lower end portion 156 which forms a diametrically opposite, laterally opening recess 158 at the lower end of the module. This recess is bounded at its inner side by two walls 160 and 162 of the housing end portion 156. These walls parallel the longitudinal axis of the optics module and are disposed at an obtuse angle relative to one another. Filme window 136 is a relatively large rectangular window which is mounted in the wider wall 160. The scene beam diverging housing 138 is mounted in the narrow wall 162.

The holographic film cassette 152 is mounted within the lower end portion 156 of the optics module 114, directly behind the window 136 and is accessible for removal and replacement by removal of a closure 163. That portion of the cassette film 134 which is exposed for holographic recording is located in a plane parallel to the window. Scene beam prism 148 is also located within the module end portion 156 behind the lens 138 in a position such that the diffuse divergent scene beam emerging through the lens illuminates the borehole wall surface region which is visible to the film 134 through the window 136 and recess 158.

From the description to this point, it will be understood that the laser 123, optics 128, and the recording medium 134 together constitute a holographic recording system which is designated in its entirety by the reference numeral 163. Each time the lase of this holographic recording system is pulsed, the holographic film 134 is illuminated directly by the reference beam 130 and simultaneously by light of the scene beam 132 which is reflected from the wall of the borehole 102, through the film window 136, to the film. A hologram of the borehole wall is thereby recorded on the film.

Turning now to the drill module 116, which constitutes the subject matter of this invention, the latter comprises drilling means 164 for drilling a stress relief hole 166 in the wall of the borehole 102 approximately at the center of the surface region of the bore which is visible to and holographically recorded on the film 134. This drilling means includes a drill head 168 supporting a drill 170 with its axis normal to the plane of the film window 136 and means 172 for extending and retracting the drill head into and from drilling position in front of the window 136 and extending and retracting the drill axially into and from drilling engagement with the borehole wall.

Figure 8:
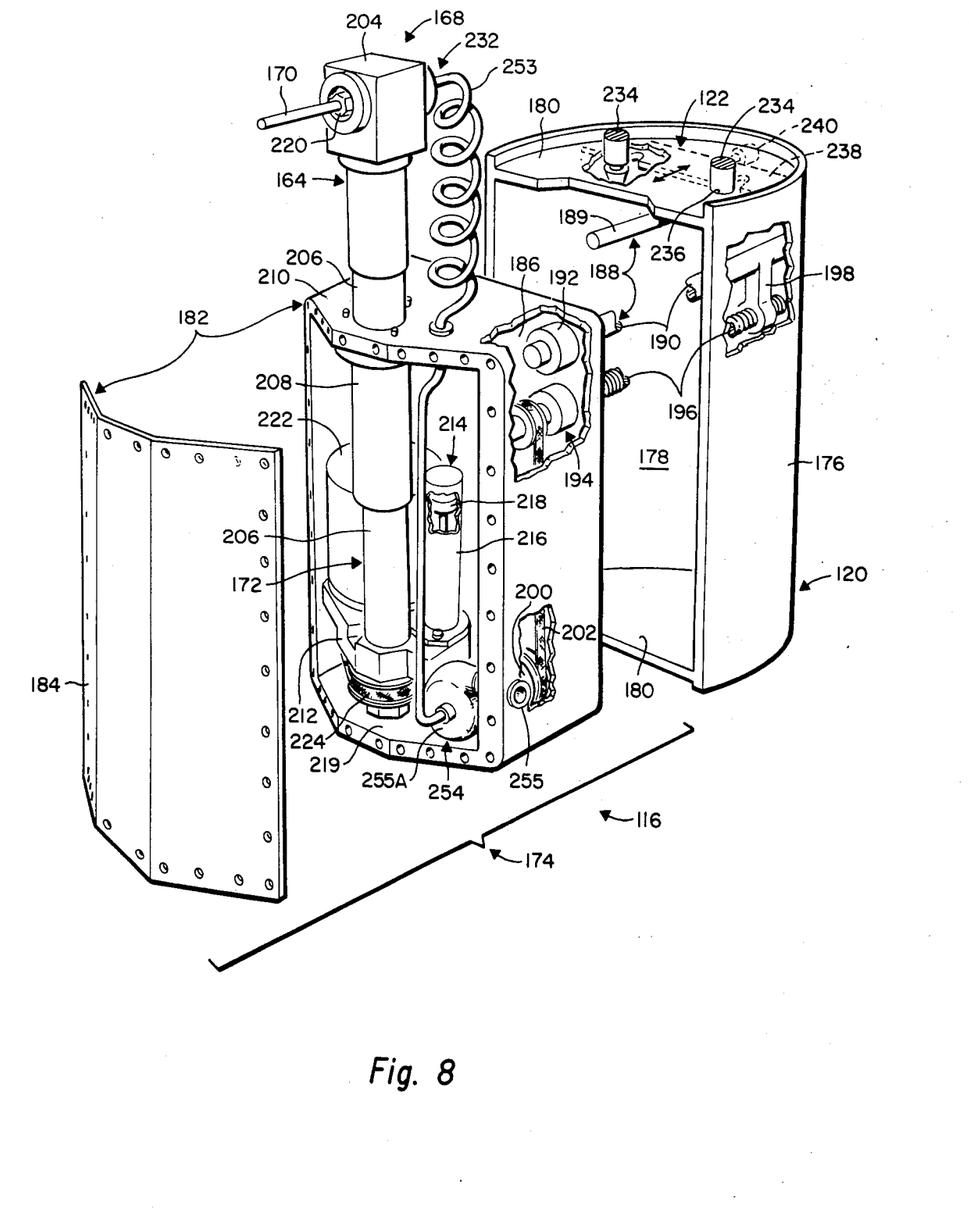
FIG. 8 is an enlarged exploded perspective view of the drill module of this invention which ie embodied in the instrument of FIGS. 4 and 5.

Referring now in more detail to the drill module 116 of this invention, and to FIGS. 7 through 9 of the drawings, the module comprises the module housing 120 and a separate drill unit 174. The module housing 120 has a cylindrically curved sidewall 176 defining an opening 178 in one side of the housing and end walls 180 rigidly joined to the ends of the sidewall, such that the housing has a laterally open shell-like configuration. The drill unit 174 has a sealed housing 182 positioned within the module housing 120. The side of the inner drill unit housing 182 facing the opening 178 in the outer module housing 120 has an opening closed by a generally gable-shaped removable cover 184. At the opposite side of the inner housing is a flat wall 186 which faces the cylindrically curved sidewall 176 of the outer housing.

The inner drill unit housing 182 is sized to pass through the opening 178 in the outer module housing 120 and is supported in the latter housing by means 188 for movement toward and away from the opening along a direction line normal to the axis of the outer housing. Supporting means 188 comprises a pair of shafts 189 and 190 which are rigidly fixed at one end to the outer housing 120 and extend slidably through bearings 192 carried by the inner housing 182. An actuator 194, hereafter referred to in places as a horizontal actuator, is provided for driving the inner housing back and forth relative to the outer housing. Actuator means 194 comprises a lead screw mechanism including a lead screw 196 which is journalled in the inner housing and extends from its wall 186 along side and parallel to the inner housing support shaft 190. Fixed to the latter shaft is a nut 198 through which the lead screw passes, such that the inner housing is movable back and forth relative to the outer housing by rotation of the lead screw. Lead screw 196 is driven in rotation by a reversible motor 200 which is mounted within the inner housing and coupled to the inner end of the screw by a belt drive 202. The inner housing is sealed to the supporting shafts 189 and 190 and lead screw 196 by seals (not shown).

As noted earlier, the drill module 116 comprises drilling means 164 including a drill head 168 and drill 170 and means 172 for extending and retracting the drill head into and from drilling position in front of the optics module window 136 and into and from drilling engagement with the wall of the borehole 102. As will appear from the ensuing description, the extension and retraction means 172 is formed in part by the actuator means or lead screw mechanism 194 which operates to extend and retract the drill 170 into and from drilling engagement with the borehole wall.

Drill head 168 comprises a generally cube-shaped housing 204 rigidly mounted on the upper end of a cylindrical post 206 which slides in a bearing sleeve 208 fixed to the upper end wall 210 of the inner drill unit housing 182. The lower end of the post projects below the bearing sleeve and its fixed to a supporting plate 212 within the housing 182 for vertical movement of the drill head 168, post 206, and plate 212 in unison relative to the housing. The drill head, post, and plate are raised and lowered relative to the inner housing by an actuator 214 comprising, in this instance, a double acting hydraulic cylinder actuator including a cylinder 216 fixed to the plate 212 and a piston 218 fixed to the lower end wall 219 of the inner drill housing 102. Actuator 214 is hereafter referred to in places as a vertical actuator.

Journalled in the drill head 168 for rotation on an axis parallel to the direction line of movement of the drill unit 174, relative to the module housing 120, is a chuck 220 mounting the drill 170. This drill is a hollow tubular drill which may comprise a tubular metal body with an annular diamond cutting edge consisting of diamond particles or chips embedded in the copper matrix of the body. Chuck 220 and hence drill 170 are driven in rotation by a motor 222 mounted on the supporting plate 212 and drivably coupled to the chuck through a belt drive 224 driving a shaft which extends axially through the post 206 and is coupled to the chuck through a right angle gear drive in the drill head 168.

As noted earlier, the drill module 116 is coupled to the lower end of the optics module 114, the latter having a lower recess 158 in front of the module window 136. The manner in which the drill module is coupled to the optics module will be explained presently. Suffice it to say at this point that the drill module is coupled to the optics module in a position such that the drill head 168 is aligned with the optics module recess 158. The drill head is vertically movable by the drill module actuator 214 between a lower retracted holographic recording position shown in full lines in FIG. 9 and an upper extended drilling position shown in broken lines in the figure. In its upper extended drilling position, the drill head is located in front of the optics module window 136 with the axis of the drill 170 approximately normal to and passing through the approximate center of the window. In its lower retracted recording position, the drill head is located below the level of the window.

During operation of the stress logging instrument 100, as described to this point, assuming that the instrument is positioned in the borehole 102, as shown in FIG. 4, the holographic system 163 is initially operated with the drill head 168 in its lowered retracted position to record on the recording medium 134 a first hologram of the wall of the borehole 102. The drill head is then extended to its raised drilling position by the vertical actuator 214, after which the horizontal actuator 194 is operated to extend the drilling unit 174 outwardly from the drill module housing 120 toward the wall of the borehole 102 opposite the optics module window 136 while the drill 170 is being driven by its motor 222, thereby to extend the drill axially into drill engagement with the wall. The drill is thus fed into the wall to drill a stress relief hole in the wall within the wall region which was initially holographically recorded on the recording medium 134. Thereafter, the horizontal actuator is reversed retract the drill from the wall and the vertical actuator is reversed to retract the drill head to its lower recording position. Finally, the holographic system 163 is again operated to record a second hologram of the borehole wall on the recording medium 134. As explained earlier, the resulting double exposure hologram constitutes a holographic interferogram which may be reconstructed to yield a fringe pattern from which the stress field in the geological formation or structure 104 may be determined.

It will be understood by those versed in the holographic art that successful operation of the instrument 100 requires firm anchoring of the optics module 114 within the borehole 102, absolute retention of the optics module against movement during the stress relief drilling operation, and a completely clear medium between the optics module window 136 and the wall of the borehole. To these ends, the coupling means 122 joining the optics and drill modules 114 and 116 are releasable, as mentioned earlier and explained in more detail below, to permit mechanical de-coupling of these modules during the drilling operation and thereby prevent the drilling operation from causing vibration and shifting of the optics module. In addition, the instrument is equipped with means 226 for firmly anchoring the modules in the borehole, means 228 for sealing the instrument to the wall of the borehole 102 at opposite sides of the borehole wall region of interest, i.e. the wall region whose stress field is to be holographically determined, means 230 for flushing the space between the seals to provide within this space a clear medium through which the wall region is clearly exposed to the holographic recording medium 134, and means 232 for continuously evacuating the debris produced during the stress relief drilling operation to prevent this debris from obscuring the wall region from the recording medium.

The illustrated coupling means 122 for releasably joining the optics and drill modules 114 and 116 comprises a pair of pins 234 which project from the lower end of the optics module through holes 236 in the upper end wall 180 of the drill module housing 120. The lower projecting ends of these pins are circumferentially grooved to receive a latch plate 238. Latch plate 238 is mounted on the underside of the housing end wall for extension into and retraction from a position of latching engagement within the pin grooves, wherein the optics and drill modules are coupled end to end, as shown. The latch plate is movable between its extended and retracted positions by a fluid pressure actuator 240.

The instrument anchoring means 226 comprises fixed pads 242 on the optics and control modules 114 and 118 for seating against one side of the borehole wall and fluid pressure actuators 244 opposite and between the pads on each module having plungers 246 for seating against the opposite side of the borehole wall. When raising and lowering the instrument from and into the borehole 102, the actuator plungers 246 are retracted from engagement with the wall to permit the instrument to move freely up and down in the hole. During operation of the instrument in the borehole, the actuators 244 are pressurized to extend their plungers 246 outwardly against the borehole wall and thereby urge the fixed pads 242 against the opposite side of the wall to firmly anchor the instrument in position, all as explained in more detail shortly.

Sealing means 228 comprises a pair of inflatable sealing rings 247 surrounding and secured to the optics module 114 and the control module 118. These rings are normally contracted to permit raising and lowering of the instrument in the borehole. After anchoring the instrument in the hole, the seal rings are internally pressurized to expand the rings into sealing engagement with the wall of the borehole, thereby sealing off the space 248 between the two rings from the remainder of the borehole.

Flushing means 230 is provided for flushing the interseal space 248 prior to operation of the instrument to provide a clear medium within the space through which the wall region of interest of the borehole may be clearly holographically recorded. This flushing means comprises flushing supply ports 250 opening from a flushing supply manifold (not shown) within the instrument at one end of the space 248 and flushing exhaust ports 252 opening to a flushing exhaust manifold (not shown) within the instrument. During operation of the instrument in the borehole 102, a clear flushing fluid is circulated through the space 248 from the supply ports 250 to the exhaust ports 252 to expose with maximum clarity the wall region of the borehole to be holographically recorded to the recording medium 134 through the instrument window 136. The flushing fluid may be supplied to the flushing supply manifold from the surface through a hose (FIG. 11) extending along the hoist cable 106 and exhausted from the exhaust manifold into the borehole above the instrument through an exhaust passage (not shown) containing a check valve, if necessary, to prevent backflow of fluid from the borehole into the space 248. If the borehole 102 is a dry hole, the flushing fluid may be a gas such as air. A clear liquid such as water may be utilized as the flushing fluid if the borehole contains a liquid.

Rather than flushing the space 248 with a separate flushing fluid, the fluid within the space may be clarified by recirculating the latter fluid from the space, through a filter within the instrument, back to the space until the fluid is sufficiently clear to permit holographic recording operation of the instrument.

The chip evacuation means 232 comprises a flexible hose 253 connecting the rear end of the hollow drill 170 to a filter unit 254 within the drill unit 174. This filter unit includes a pump (not shown) driven by the drill motor 222 for sucking in through the drill 170 drill chips and liquid, if any, or air in the well bore, and a filter through which the liquid or air is discharged back to the well bore through an outlet 255. The filter removes the drill chips and other solids and is accessible for cleaning by removal of the drill unit cover 184 and the filter unit cover 255a.

Operation of the instrument in a borehole filled with water or other liquid may produce on the instrument hydrostatic forces which are too large to be sustained solely by the structural strength of the instrument housings. In this case, it will be necessary to internally pressurize the the instrument to partially or totally balance the external hydrostatic pressure.

Figure 11:
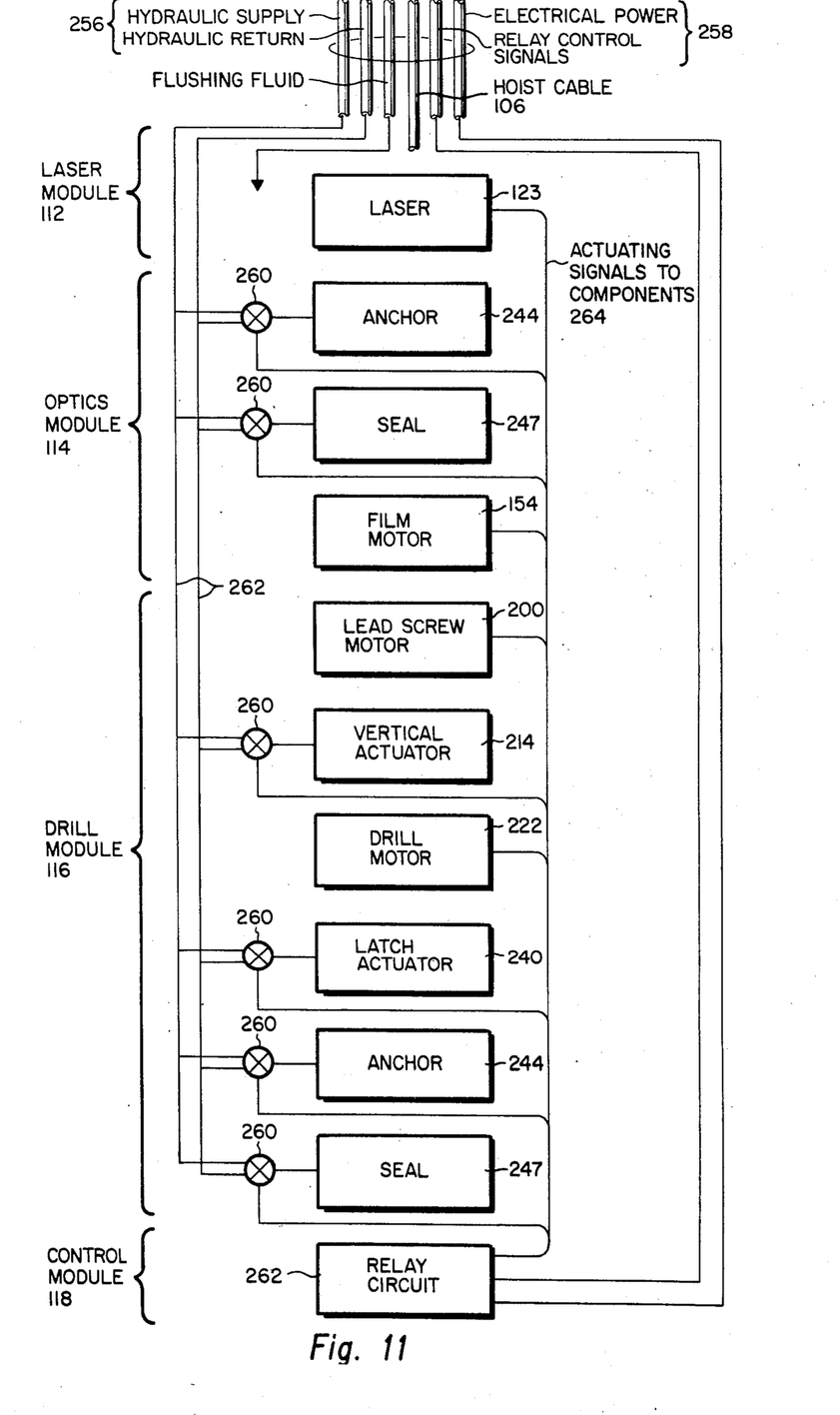
FIG. 11 is an electrical and hydraulic circuit diagram of the instrument.

At this point, it will be understood that the instrument 100 comprises a number of electrically and fluid powered components which must be selectively operated. These components are the laser 123, the film advance motor 154, the lead screw drive motor 200 and drill drive motor 222 of the drill module 116, the vertical actuator 214 of the drill module, the latch plate actuator 240 for the optics-drill module coupling means 122, and the instrument anchor actuators 244 and inflatable seal rings 247. The pressurized working fluid for the fluid powered components, the electrical power for the electrically powered components are furnished by fluid and electrical power sources contained within the surface control van 110 and connected to the instrument 100 through hoses 256 and an electrical cable 258 extending along the hoist cable 106 as shown in FIG. 11. Within the instrument are solenoid valves 260 for controlling fluid flow to the fluid powered components and a relay circuit 262 which are connected through electrical lines 264 to the various valves and electrical components and through the electrical cable 258 to controls and the electrical power source in the van for selective operation of the components by the surface controls to effect the instrument operation described below. Those portions of the hoses 256, cable 258, and lines 262 which extend across the interface between the optics and drill modules 116 and 118 are made sufficiently flexible to attain mechanical isolation of these modules by release of the coupling means 122, in the manner explained earlier.

Operation of the instrument 100 will not be summarized. The instrument is internally pressurized, if necessary, and lowered to the desired depth in the borehole 102. Upon arrival at this depth, the anchor actuators 244 are pressurized to firmly anchor the instrument in the borehole and the seal rings 247 are pressurized to seal the instrument to the wall of the hole. The latch plate actuator 240 is pressurized to retract the latch plate 238 from engagement with the optics module latch pins 235 and thereby mechanically decouple the drill module 116 from the optics module 114. The space 248 between the seal rings 247 is then flushed in the manner explained earlier to provide a clear medium between the wall of the borehole and the optics module window 136. At this point, the instrument is conditioned for operation through its holographic recording cycle.

In the course of this recording cycle, the laser 123 is initially pulsed to record on the holographic recording medium 134 a first hologram of the borehole wall region opposite the window 136 of the optics module 114. This recording is made with the drill head retracted, both vertically and horizontally to its solid line position of FIG. 9. Following recording of this first hologram, the vertical drill actuator 214 is pressurized to raise the drill to its broken line position of the latter figure. The lead screw and drill motors 200 and 222 are then operated to drive the drill 170 in rotation and drive the lead screw 196 in a direction to advance the rotating drill 164 against the borehole wall and thereby drill a stress relief hole 166 in the wall. The chips and other debris produced during this drilling operation are evacuated through the drill, as explained earlier. Thereafter, the lead screw motor 200 is reversed to drive the lead screw in the opposite direction to retract the drill from the borehole wall and the drill head is returned to its solid line retracted position by the vertical drill actuator 214. The laser 123 is then pulsed a second time to record a second hologram of the borehole wall on the recording medium 134. As noted earlier, these two holograms constitute a double exposure hologram or interferogram which may be reconstructed to form a holographic image with fringe patterns (FIG. 2) which represent the displacements that occur in the borehole wall as a result of drilling the stress relief hole and which may be interpreted to yield data defining the stress field in the wall.

In some applications, a single interferogram may yield sufficient stress field data. In other cases, it may be necessary to record several interferograms of circumferentially spaced regions of the borehole wall. This is accomplished by recoupling the optics and drill modules, releasing the instrument anchor means and sealing means, rotating the instrument by the hoist cable to a new recording position, and then repeating the operation procedure described above.

We claim:

1. A drill module for a holographic borehole stress measuring instrument having an elongate holographic optics module, comprising:
   an elongate support housing;
   coupling means on an end of said housing for releasably connecting the housing to one end of said optics module in end-to-end relation with said optics module;
   a drill head at said one housing end for supporting a drill with its axis transverse to the longitudinal axis of said housing;
   means supporting said drill head on said housing for extension and retraction relative to said housing along a first direction line parallel to said housing axis and along a second direction line parallel to said drill axis; and
   means for extending said drill head along said first direction line and then extending the drill head along said second direction line and thereafter retracting said drill head along said second direction line and then retracting the drill head along said first direction line.

2. A drill module for a holographic borehole stress measuring instrument having an elongate holographic optics module comprising;
   an elongate support housing open at one side;
   coupling means on one end of said housing for releasably connecting the housing to one end of said optics module in end-to-end relation with said optics module;
   a drill unit including a housing disposed within said open side of said support housing with an end of said drill unit housing adjacent said one end of said support housing, a drill head at said one end of said drill unit housing externally of said support housing for supporting a drill for rotation with its axis transverse to the longitudinal axis of the support housing, and means mounting said drill head on said drill unit housing for extension beyond and retraction toward said one end of said latter housing along a first direction line parallel to said support housing axis;
   means supporting said drill unit housing on said support housing for retraction into and extension from said support housing through said open housing side along a second direction line parallel to said drill axis;
   means for extending said drill head along said first direction line and then extending said drill unit housing along said second direction line and thereafter retracting said drill unit housing along said second direction line and then retracting said drill head along said first direction line; and
   means for driving the drill in rotation in said drill head.

3. A drill unit according to claim 2 wherein:
   said drill head mounting means comprises a post extending slidably through said one end of said drill unit housing parallel to said first direction line and mounting said drill head at the outer end of the post; and
   said extension and retraction means comprises actuator means within said drill unit housing and operatively connected to the inner end of said post for extending and retracting said post axially relative to the latter housing.

4. A drill module according to claim 3 wherein:
   said drill driving means comprises a chuck in said drill head for holding the drill, a motor within said drill unit housing, and drive means extending axially through said post drivably connecting said motor and chuck.

5. A drill unit according to claim 4 including:
   means mounting said motor on the lower end of said post for axial movement with the post.

6. A drill module according to claim 2 wherein:
   said extension and retraction means comprises actuator means connecting said housings for retracting and extending said drill unit housing along said second direction line into and from said support housing.

7. A drill module according to claim 6 wherein:
   said last mentioned actuator means comprises a lead screw rotatably fixed to said drill unit housing and threaded in a nut on said support housing, and a motor in said drill unit housing for driving said lead screw.

8. A drill unit according to claim 7 wherein:

said drill head mounting means comprises a post extending slidably through said one end of said drill unit housing parallel to said first direction line and mounting said drill head at the outer end of the post; and said extension and retraction means comprises actuator means within said drill unit housing and operatively connected to the inner end of said post for extending and retracting said post axially relative to the latter housing.

9. A drill module according to claim 8 wherein:

said drill driving means comprises a chuck in said drill head for holding the drill, a motor within said drill unit housing, and drive means extending axially through said post for drivably connecting said motor and chuck.

10. A drill unit according to claim 9 including:

means mounting said motor on the lower end of said post for axial movement with the post.

11. A drill module according to claim 10 including:

means for evacuating drilling chips from the drill tip.

* * * * *